(12) United States Patent
Pillai et al.

(10) Patent No.: US 8,883,212 B2
(45) Date of Patent: Nov. 11, 2014

(54) TOOTH FILM FORMULATIONS

(75) Inventors: Shyamala Pillai, Piscataway, NJ (US); Guofeng Xu, Plainsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/349,694

(22) PCT Filed: Nov. 7, 2011

(86) PCT No.: PCT/US2011/059544
§ 371 (c)(1),
(2), (4) Date: Apr. 4, 2014

(87) PCT Pub. No.: WO2013/070184
PCT Pub. Date: May 16, 2013

(65) Prior Publication Data
US 2014/0242001 A1  Aug. 28, 2014

(51) Int. Cl.
| | | |
|---|---|---|
| A61K 8/73 | (2006.01) | |
| A61K 8/81 | (2006.01) | |
| A61Q 11/00 | (2006.01) | |
| A61Q 17/00 | (2006.01) | |
| A61K 8/29 | (2006.01) | |
| A61K 8/21 | (2006.01) | |

(52) U.S. Cl.
CPC .............. A61K 8/8158 (2013.01); A61K 8/731 (2013.01); A61Q 17/00 (2013.01); A61Q 11/00 (2013.01); A61K 8/29 (2013.01); A61K 8/21 (2013.01)
USPC ......................... 424/487; 424/401; 433/217.1

(58) Field of Classification Search
USPC .............................................. 424/61, 53, 401
See application file for complete search history.

(56) References Cited

U.S. PATENT DOCUMENTS

| | | | |
|---|---|---|---|
| 5,747,017 A * | 5/1998 | Nichols et al. .................. 424/61 |
| 6,261,576 B1 | 7/2001 | Fishman | |
| 6,818,205 B2 | 11/2004 | Reinehr et al. | |
| 7,476,697 B2 | 1/2009 | Patacca et al. | |
| 2007/0122360 A1 | 5/2007 | Oniki et al. | |
| 2008/0318833 A1* | 12/2008 | Jermann et al. .................. 512/2 |

FOREIGN PATENT DOCUMENTS

| | | |
|---|---|---|
| WO | WO 2007/068703 | 6/2007 |
| WO | WO 2009/140334 | 5/2009 |
| WO | WO 2011/042897 | 4/2011 |
| WO | WO 2011/062805 | 5/2011 |

OTHER PUBLICATIONS

International Search Report and the Written Opinion issued in International Application No. PCT/US2011/59544 mailed Sep. 4, 2012 (WO).
Written Opinion of the International Preliminary Examining Authority issued in International Application PCT/US2011/59544 mailed Nov. 19, 2013 (WO).

* cited by examiner

*Primary Examiner* — Walter Webb
(74) *Attorney, Agent, or Firm* — Anne Louise St. Martin

(57) ABSTRACT

The invention provides novel dental film-forming compositions, comprising i. an acrylate/octylacrylamide copolymer, ii. one or more alkyl cellulose ethers, and iii. a solvent, and optionally further comprising whitening materials and/or active agents, together with method for using the same.

13 Claims, No Drawings

TOOTH FILM FORMULATIONS

FIELD OF THE INVENTION

The present invention relates to novel film compositions for application to teeth to provide whitening, and other benefits.

BACKGROUND OF THE INVENTION

Most tooth whitening systems in use today contain peroxide or other bleaching material. Peroxide-based products may present formulation difficulties, due to the volatility and reactivity of hydrogen peroxide, and many countries strictly regulate peroxide levels in tooth whitening products.

There is also a need to protect the teeth from bacteria and plaque formation, and to provide sustained delivery of active agents, for example fluoride, antibacterial agents, and remineralization agents.

Polymer delivery systems for application to the teeth have in general not proved sufficiently durable to remain on the teeth for extended periods. The teeth are physically abraded by brushing and chewing and are moreover exposed to a wide range of temperatures and pH levels as a result of eating and drinking. Under ordinary conditions, therefore, most polymers will not remain on the teeth for very long. Moreover, it is desirable that the polymers themselves to not readily take up stain or otherwise discolor the teeth.

There is an unmet need in the art for a delivery system that can provide whitening particles and other active ingredients to the teeth and protect the teeth from plaque and biofilm formation for extended periods.

BRIEF SUMMARY OF THE INVENTION

We have discovered that formulations comprising acrylate/octylacrylamide copolymers are suitable for application to the teeth, that they are easily applied and that they are more durable than other polymer systems, even in the face of brushing and acid challenges, thus making them suitable vehicles for delivery and sustained application of whitening particles and/or active agents to the teeth and for protecting the teeth from staining and from biofilm and plaque formation, which could otherwise lead to tooth decay and gingivitis.

In one embodiment, the invention provides a dental film-forming composition comprising
  i. an acrylate/octylacrylamide copolymer, for example 2-propenoic acid, 2-methyl-, 2-methylpropyl ester, polymer with 2-propenoic acid and N-(1,1,3,3-tetramethylbutyl)-2-propenamide, (e.g., DERMACRYL 79®), e.g. in an amount by weight of 5-30%, e.g. greater than 10%, for example about 20%;
  ii. one or more alkyl cellulose ethers, e.g., ethyl cellulose, e.g., in an amount by weight of 1-20%, e.g., about 5%;
  iii. an orally acceptable solvent, for example ethanol.
The formulation may be applied to provide a film which protects against staining and bacteria, and/or may optionally further comprise one or more of the following: whitening materials, for example comprising, titanium dioxide, zinc oxide, hydroxylapatite, or combinations thereof; one or more antibacterial agents, e.g., triclosan; and/or one or more fluoride ion sources, e.g., sodium monofluorophosphate; calcium sources, e.g. calcium carbonate; basic ammo acids, e.g. arginine in free or salt form; or other active agents.

The invention moreover provides methods of whitening and/or protecting the teeth from stain or bacterial damage and/or delivering an active ingredient, comprising applying a formulation of the invention to the teeth.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred, embodiment(s) is merely exemplary in nature and is in no way intended to limit the invention, its application, or uses.

By "acrylate/octylacrylamide copolymer" is meant a copolymer of octylacrylamide (for example N-(1,1,3,3-tetramethylbutyl)-2-propenamide) and one or more monomers selected from acrylic acid, methacrylic acid and their simple esters. In a particular embodiment, the acrylate/octylacrylamide copolymer is 2-Propenoic acid, 2-methyl-, 2-methylpropyl ester, polymer with 2-propenoic acid and N-(1,1,3,3-tetramethylbutyl)-2-propenamide (CAS 129702-02-9) for example DERMACRYL® 79 (commercially available from National Starch or AkzoNobel).

By "alkyl cellulose ether" is meant a lower alkyl ether of cellulose, for example ethyl cellulose, e.g. ethyl cellulose having a degree of ethoxylation of 45-50% and a viscosity of from 3-70 mPa·sec (5% solution at 25° C. measured in Ubbelohde viscometer), e.g. from the Ethocel® product line available from The Dow Chemical Company, e.g. Ethocel® E7, Ethocel® E22 or Ethocel® E50. The alkyl of the alkyl cellulose ether is optionally hydroxy-substituted, e.g., hydroxypropyl cellulose.

By "varnish" is meant a traditional varnish, comprising a drying oil, a resin, and a thinner or solvent, as well as shellac, and lacquer.

By "orally acceptable" is meant safe for use in the mouth at levels required.

The invention thus provides, in a first embodiment, a dental film-forming composition (Composition 1), comprising
  i. an acrylate/octylacrylamide copolymer,
  ii. one or more alkyl cellulose ethers, and
  iii. a solvent;
for example
  1.1. Composition 1 wherein the acrylate/octylacrylamide copolymer is 2-propenoic acid, 2-methyl-, 2-methylpropyl ester, polymer with 2-propenoic acid and N-(1,1,3,3-tetramethylbutyl)-2-propenamide;
  1.2. Composition 1 or 1.1 wherein the acrylate/octylacrylamide copolymer is present in an amount by weight of 5-30%;
  1.3. Any of the preceding compositions wherein the acrylate/octylacrylamide copolymer is present in an amount greater than 10% by weight;
  1.4. Any of the preceding compositions wherein the acrylate/octylacrylamide copolymer is present in an amount of about 20% by weight;
  1.5. Any of the preceding compositions wherein the alkyl cellulose ether is ethyl cellulose;
  1.6. Any of the preceding compositions wherein the alkyl cellulose ether is a combination of ethyl cellulose and a hydroxyalkyl cellulose ether, e.g., hydroxypropyl cellulose;
  1.7. Any of the foregoing compositions comprising ethyl cellulose and hydroxypropyl cellulose in a ratio of 2:1 to 30:1, e.g. about 4:1;

1.8. Any of the foregoing compositions wherein the alkyl cellulose ether component present in an amount by weight of 1-20%;
1.9. Any of the foregoing compositions comprising; ethyl cellulose in an amount of 1-10%. e.g., 2-5%;
1.10. Any of the foregoing compositions comprising hydroxypropyl cellulose in an amount of 0.01-1%, e.g., approximately 0.25% or 0.5%;
1.11. Any of the foregoing compositions comprising about 2% ethyl cellulose and about 0.5% hydroxypropyl cellulose;
1.12. Any of the foregoing compositions wherein the orally acceptable solvent is ethanol;
1.13. Any of the foregoing, compositions comprising a whitening material;
1.14. Any of the foregoing compositions comprising an opaque whitening material;
1.15. Any of the foregoing compositions comprising a whitening material selected from titanium dioxide, zinc oxide, hydroxylapatite, and combinations thereof;
1.16. Any of the foregoing compositions comprising an effective amount of an antibacterial agent, e.g., triclosan;
1.17. Any of the foregoing compositions comprising a fluoride ion source, e.g., sodium monofluorophosphate;
1.18. Any of the foregoing compositions comprising a calcium source, e.g. calcium carbonate;
1.19. Any of the foregoing compositions comprising, a basic amino acid, e.g. arginine in free or salt form;
1.20. Any of the foregoing compositions in liquid form;
1.21. Any of the foregoing compositions in the form of gel;
1.22. Any of the foregoing compositions which is free from varnish;
1.23. Any of the foregoing compositions comprising the following ingredients by weight
   ethyl cellulose 1-7%, e.g., 2-5%,
   hydroxypropyl cellulose 0.1-0.75%, e.g., about 0.25-0.5%,
   acrylate/octylacrylamide copolymer 10-30%, e.g., about 20%,
   ethanol in an amount sufficient to solubilize the ingredients,
   water, and
   optionally whitening material in an amount sufficient to provide a white color to the teeth upon application.
2. In a further embodiment, the invention provides a package comprising any of the foregoing compositions together with an applicator for applying the composition to the teeth.
3. In a further embodiment, the invention provides a method of protecting the teeth from staining or bacteria comprising applying any of the foregoing compositions to the teeth.
4. In a further embodiment, the invention provides the use of any of the foregoing compositions in the manufacture of an oral care product for protecting the teeth from staining or bacteria.

As used throughout, ranges are used as shorthand for describing each and ever value that is within the range. Any value within the range can be selected as the terminus of the range. In addition, all references cited herein are hereby incorporated by referenced in their entireties. In the event of a conflict in a definition in the present disclosure and that of a cited reference, the present disclosure, controls.

Unless otherwise specified, all percentages and amounts expressed herein and elsewhere in the specification should be understood to refer to percentages by weight. The amounts given are based on the active weight of the material.

EXAMPLE 1

Formulation Effectiveness Comparison

Test formulations are prepared as follows:

TABLE 1

| | Film forming compositions | | | | | |
|---|---|---|---|---|---|---|
| Ingredient | A | B | C | D | E | F |
| E7 | 5 | 5 | 5 | 5 | 5 | 5 |
| HPC | 0.25 | 0.25 | 0.25 | 0.25 | 0.25 | 0.25 |
| A/O | 0 | 10 | 20 | 0 | 0 | 0 |
| EPO | 0 | 0 | 0 | 10 | 20 | 0 |
| RL100 | 0 | 0 | 0 | 0 | 0 | 10 |
| EtOH | Qs | Qs | Qs | Qs | Qs | qs |
| Total | 100 | 100 | 100 | 100 | 100 | 100 |

E7 - Ethyl cellulose (Ethocel ® E7 (Dow))
HPC - Hydroxypropyl cellulose
A/O - Acrylate/octylacrylamide copolymer (DERMACRYL ® 79)
EPO - Butyl methacrylate-(2-dimethyl aminoethyl)methacrylate-methylmethacrylate copolymer
RL 100 - Ammonium methacrylate copolymer Percent of Coating Removed on Mechanical and Acid Challenge:

Enamel blocks are stained by first exposing to peptide 20 uM peptide (DE 62) and then coloring with 0.5% Red Iron Oxide dispersion in 10 mM phosphate buffer. Each stained enamel block is treated with 1 ml of the formula for 2 min and allowed to air dry. For wet swabbing a Styrofoam swab is wetted with water and used for the swipe test. For brushing challenge, 1:2:toothpaste:water slurry is prepared and used for the brushing. The toothpaste is a commercial toothpaste (COLGATE Max Fresh®). Each block is brushed for 15 sec. For the acid challenge, the treated blocks are exposed to acid, pH=3.8 for 5 min and again brushed with toothpaste for 15 sec.

| Product | Wet swab 5 strokes | Wet swab 10 strokes | Brushing with 1:2 toothpaste slurry | Acid challenge 5 min exposure, pH 3.8 |
|---|---|---|---|---|
| 0% A/O (A) | 5% | 15% | 100% | NA |
| 10% A/O (B) | 0 | 0 | 5% | 10% |
| 20% A/O (C) | 0 | 0 | 0 | 0 |
| 10% EPO (D) | 5% | 10% | 25% | 95% |
| 20% EPO (E) | 0 | 0 | 10% | 50% |
| 10% RL100 (F) | 0 | 0 | 5% | 10% |

Percent of Coating Removed on Saliva Exposure for 5 Hrs @ 37 C:

To Simulate intra-oral conditions, each treated (coated) block is treated with 1 ml clarified whole saliva and incubated at 37° C. for five hours. Post treatment, each block is again tested for various challenge tests and percent removal of the coating is recorded. So in the table below, the lower the percentage removed, the more durable and effective the coating is.

| Product | Wet swab 10 strokes | Brushing with 1:2 MF slurry (% coating removed) | Acid challenge 5 min exposure, pH 3.8 (% coating removed) |
| --- | --- | --- | --- |
| 0% A/O (A) | 100 | NA | NA |
| 10% A/O (B) | 0 | 5 | 15 |
| 20% A/O (C) | 0 | 0 | 0 |
| 10% EPO(D) | 20 | 60 | 85 |
| 20% EPO (E) | 35 | 45 | 70 |
| 10% RL100 (F) | 10 | 25 | 35 |

Each block is exposed to all the above three challenges serially. Only the formulation comprising acrylate/octylacrylamide copolymer at 20% (C) was impervious to brushing, acid and saliva, although the formulation comprising acrylate octylacrylamide copolymer at 10% (B) performed nearly as well.

Stain Test:

This test is designed to verify if the coated surface attracts stain. Bovine enamel blocks are coated with prototype solutions, and on drying are exposed to tea-coffee stain (1:2 ratio) for 30 min at 40° C. The whiteness level is measured both before and after exposing to the staining solution.

At 40° C., the coating from A and F do not survive hot temp condition and the coating is completely removed without any mechanical force. With EPO (D and E), 30-50% of the coating came off after treatment, again without any mechanical force, and the coating, which remains is much darker, indicating that the coating absorbed stain from the tea-coffee staining solution. Only prototypes B and C with acrylate/octylacrylamide copolymer survive hot temperature conditions, and these prototypes moreover do not absorb stain. Accordingly, the formulations are useful to prevent staining.

It is further shown that the presence of ethyl cellulose and hydroxypropyl cellulose, which act as dispersants, and in the case of ethyl cellulose, as additional film forming agents, enhance the stain-protecting effect of the acrylate/octylacrylamide copolymer formulation, possibly by increasing hydrophobicity of the film. As seen above, with formulation A, ethyl cellulose and hydroxypropyl cellulose by themselves are wholly ineffective as they do not adhere to the teeth, so this is a surprising synergy. The control in this experiment is a hare enamel block; a more negative L value indicates increased staining.

TABLE 2

| Acrylate/octylacrylamide copolymer formulation with varying dispersants | | |
| --- | --- | --- |
| Ethyl cellulose | Hydroxypropyl cellulose | Staining (L value) |
| 2% | 0.5% | −4 |
| 5% | 0% | −1 |
| 5% | 0.25% | 0 |
| | | Control: −8 |

It is also noted that the formulations comprising ethyl cellulose/hydroxypropyl cellulose as dispersants have a good shine and smooth feel compared to the other formulations.

EXAMPLE 2

Formulation Stability Comparison

Drying time and stability are also evaluated. Stability is evaluated using optical centrifugation as a predictive model for physical stability. Formulations are injected into small centrifuge tubes. The samples are placed horizontally on rotating plate and spun/centrifuged at high speed (about 2400 rpm) for about 3 days. Light emitted from a light source travels through cell and the transmitted light is recorded by a detector. The percentage of light transmitted is profiled over time, and there is an established correlation between the degree of separation (as indicated by increased light transmittance) and stability on the shelf. A stability score of 3 or less is considered acceptable. Some of the formulations tested have stability that would correspond to about 6-12 months shelf stability.

Formulations containing varying amounts of dispersant are prepared, as set forth in Table 3a, 3b and 3c, units given as milliliters/10 mL total volume:

TABLE 3a

| | 1 | 2 | 3 | 4 |
| --- | --- | --- | --- | --- |
| Ethyl cellulose (Ethocel ® E7) | 0.2 | 0.2 | 0.5 | 0.5 |
| Hydroxypropyl cellulose | 0.025 | 0.05 | 0 | 0.025 |
| A/O (20%) | 2 | 2 | 2 | 2 |
| TiO2 (3%) | 0.6 | 0.6 | 0.6 | 0.6 |
| Ethanol | 7.175 | 7.15 | 6.9 | 6.875 |

TABLE 3b

| | 5 | 6 | 7 | 8 |
| --- | --- | --- | --- | --- |
| Ethyl cellulose (Ethocel ® E22) | 0.2 | 0.2 | 0.5 | 0.5 |
| Hydroxypropyl cellulose | 0.025 | 0.05 | 0 | 0.025 |
| A/O (20%) | 2 | 2 | 2 | 2 |
| TiO2 (3%) | 0.6 | 0.6 | 0.6 | 0.6 |
| Ethanol | 7.175 | 7.15 | 6.9 | 6.875 |

TABLE 3c

| | 9 | 10 | 11 | 12 |
| --- | --- | --- | --- | --- |
| Ethyl cellulose (Ethocel ® E50) | 0.2 | 0.2 | 0.5 | 0.5 |
| Hydroxypropyl cellulose | 0.025 | 0.05 | 0 | 0.025 |
| A/O (20%) | 2 | 2 | 2 | 2 |
| TiO2 (3%) | 0.6 | 0.6 | 0.6 | 0.6 |
| Ethanol | 7.175 | 7.15 | 6.9 | 6.875 |

The drying times of the different formulations are measured, with a shorter drying tune being desirable:

TABLE 4

| | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| Drying Time | 1:00 | 1:45 | 1:20 | 3:00 | 1:30 | 1:45 | 2:30 | 2:00 | 2.20 | 1.00 | 1:45 | 7:00 |

The stability, measured a relative degree of separation of the components is then assessed in the optical centrifugation model to predict stability at 3 months, 6 months and 1 year, as shown in Table 5, where the numbers reflect the degree of separation, the lower numbers indicating greater stability, and 3 or less being considered stable:

TABLE 5

| Sample No. | 3 months | 6 months | 1 year |
|---|---|---|---|
| 1 | 2.60 | 3.42 | 4.41 |
| 2 | 2.50 | 3.34 | 4.33 |
| 3 | 3.33 | 4.26 | 5.17 |
| 4 | 1.80 | 2.57 | 3.36 |
| 5 | 2.42 | 3.18 | 4.01 |
| 6 | 2.09 | 2.77 | 3.57 |
| 7 | 1.80 | 5.56 | 6.05 |
| 8 | 2.07 | 2.93 | 4.10 |
| 9 | 2.11 | 2.83 | 3.65 |
| 10 | 1.58 | 2.32 | 3.07 |
| 11 | 3.58 | 6.06 | 6.07 |
| 12 | 2.22 | 5.61 | 6.02 |

Formulation 10 shows good stability, as do formulations 4, 6 and 9. Formulations exhibiting shorter drying time tend to have better stability, probably because both parameters are related to the degree of dispersion.

The invention claimed is:

1. A dental film-forming composition, comprising
   i. an acrylate/octylacrylamide copolymer, wherein the acrylate/octylacrylamide copolymer is present in an amount by weight of 5-30%,
   ii. one or more alkyl cellulose ethers, and
   iii. a solvent,
   wherein the composition is orally acceptable.

2. The composition of claim 1 wherein the acrylate/octylacrylamide copolymer is 2-propenoic acid, 2-methyl-, 2-methylpropyl ester, polymer with 2-propenoic acid and N-(1,1,3,3-tetramethylbutyl)-2-propenamide.

3. The composition of claim 1 wherein the acrylate/octylacrylamide copolymer is present in an amount greater than 10% by weight.

4. The composition of claim 1 wherein the one or more alkyl cellulose ethers comprises ethyl cellulose and hydroxypropyl cellulose.

5. The composition of claim 4 wherein the ratio of ethyl cellulose to hydroxypropyl cellulose is from 2:1 to 30:1.

6. The composition of claim 1 wherein the orally acceptable solvent is ethanol.

7. The composition of claim 1 further comprising a whitening material.

8. The composition of claim 7 wherein the whitening material is selected from titanium dioxide, zinc oxide, hydroxylapatite, and combinations thereof.

9. The composition of claim 1 comprising one or more of an antibacterial agent, a fluoride ion source, a calcium source, or a basic amino acid.

10. The composition of claim 1 comprising
    ethyl cellulose in an amount of 1-7 weight %, optionally 2-5 weight %, hydroxypropyl cellulose in an amount of 0.1-0.75 weight %, optionally 0.25-0.5 weight %,
    the acrylate/octylacrylamide copolymer is present in an amount of 10-30 weight %, optionally 20 weight %, and
    ethanol in an amount sufficient to solubilize the ingredients, and water.

11. A package comprising a composition according to claim 1 together with an applicator for applying the composition to the teeth.

12. A method of protecting the teeth from staining or bacteria comprising applying a composition of claim 1.

13. A composition of claim 1 for use in protecting the teeth from staining or bacteria.

* * * * *